United States Patent [19]

Seido et al.

[11] Patent Number: 5,801,271

[45] Date of Patent: Sep. 1, 1998

[54] 7-(N-SUBSTITUTED AMINO)-2-PHENYLHEPTANOIC ACID DERIVATIVE AND PROCESS FOR MANUFACTURING THE SAME

[75] Inventors: Nobuo Seido; Takenobu Nishikawa; Tsukasa Sotoguchi; Yoshifumi Yuasa; Takashi Miura; Hidenori Kumobayashi, all of Kanagawa, Japan

[73] Assignee: Takasago International Corporation, Tokyo, Japan

[21] Appl. No.: 895,429

[22] Filed: Jul. 16, 1997

[30] Foreign Application Priority Data

Apr. 2, 1997 [JP] Japan .................... 9-117359

[51] Int. Cl.$^6$ .................... C07C 271/06; C07C 269/06
[52] U.S. Cl. .................... 560/29; 560/12; 560/31; 560/37; 560/38; 560/39; 554/36; 548/336.1; 548/338.1
[58] Field of Search .................... 560/31, 12, 37, 560/38, 39, 29; 514/538, 541; 554/36; 548/338.1, 336.1

[56] References Cited

U.S. PATENT DOCUMENTS

| | | | |
|---|---|---|---|
| 3,406,165 | 10/1968 | Kruckenberg | 560/29 |
| 3,467,690 | 9/1969 | Chamberlin | 560/29 |
| 5,371,271 | 12/1994 | Kruger et al. | 560/136 |

*Primary Examiner*—Shailendra Kumar
*Attorney, Agent, or Firm*—Sughrue, Mion, Zinn, Macpeak & Seas, PLLC

[57] ABSTRACT

Disclosed is a 7-(N-substituted amino)-3-oxo-2-phenylheptanoate derivative, 7-(N-substituted amino)-3-hydroxy-2-phenylheptanoate derivative, and 7-(N-substituted amino)-3-benzenesulfonyloxy-2-phenylheptanoate derivative, which are quite important major intermediates for an antidepressant. The 7-(N-substituted amino)-3-oxo-2-phenylheptanoate derivative can be manufactured by condensing an enolate of phenylacetates with a 5-(N-substituted amino) pentanoate derivative.

9 Claims, No Drawings

7-(N-SUBSTITUTED AMINO)-2-PHENYLHEPTANOIC ACID DERIVATIVE AND PROCESS FOR MANUFACTURING THE SAME

BACKGROUND OF THE INVENTION

1. Field of the Invention

The present invention relates to a 7-(N-substituted amino)-2-phenylheptanoic acid derivative useful as a synthesis intermediate for an optically active methyl 2-phenyl-2-(2'-piperidinylidene)acetate derivative which is a major intermediate for an antidepressant as described below and to a process for manufacturing the 7-(N-substituted amino)-2-phenylheptanoic acid derivative.

2. Description of the Related Art

As an antidepressant, methyl threo-2-phenyl-2-(2'-piperidyl)acetate.hydrochloride (trade name: Ritalin) is commercially available in the form of racemic compounds. Also, it is known for this antidepressant that a specific stereoisomer has a pharmacological activity five times higher than that of other stereoisomers (see U.S. Pat. No. 2,957,880).

Further, structural analysis studies on methyl 2-phenyl-2-(2'-piperidinyl)acetate have progressed and the absolute configuration of an optically active form of this compound has been reported (see *J. Med. Chem.* 12, 266, 1969).

The above optically active methyl threo-2-phenyl-2-(2'-piperidyl)acetate is manufactured, for example, by the following known processes:

(1) A process in which phenylacetonitrile and 2-chloropyridine are condensed in the presence of sodium amide, followed by hydrolysis and reduction to prepare 2-phenyl-2-(2'-piperidinylidene)acetic acid amide (see U.S. Pat. No. 2,507,361). This acetic acid amide is, then separated into two kinds of racemic compounds by recrystallization. The resulting racemic compounds are then optically resolved using optically active tartaric acid, followed by hydrolysis and esterification to synthesize the above optically active compound(see U.S. Pat. No. 2,957,880).

(2) A process in which optically active chlorophenylamine is subjected to a Hofmann decomposition reaction to prepare an olefinic compound, which is then subjected to an oxidation reaction using ozone to synthesize the above optically active compound (see *J. Pharm. Sci,* 56, 1689, 1967).

However, in these processes, complicated operations are required and it is also necessary to use an optically active resolving agent and an optically active material which are both expensive.

SUMMARY OF THE INVENTION

An object of the present invention is to provide a novel 7-(N-substituted amino)-2-phenylheptanoic acid derivative.

Another object of the present invention is to provide a process for manufacturing the 7-(N-substituted amino)-2-phenylheptanoic acid derivative.

The novel compound of the present invention is the 7-(N-substituted amino)-3-(substitued)-2-phenylheptanoate derivative represented by the following formula (1):

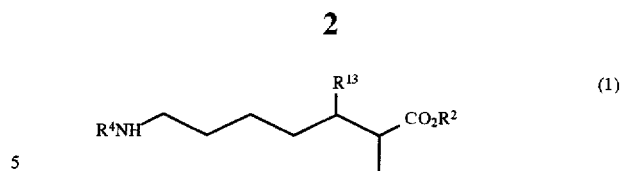

wherein $R^1$ represents a hydrogen atom, a lower alkyl group having 1 to 4 carbon atoms, or a lower alkoxy group having 1 to 4 carbon atoms; $R^2$ represents a lower alkyl group having 1 to 4 carbon atoms; and $R^{13}$ represents a keto group, a hydroxy group and a benzenesulfonyloxy group.

Preferred compound of the present invention include 7-(N-substituted amino)-3-oxo-2-phenylheptanoate derivatives represented by the following formula (2):

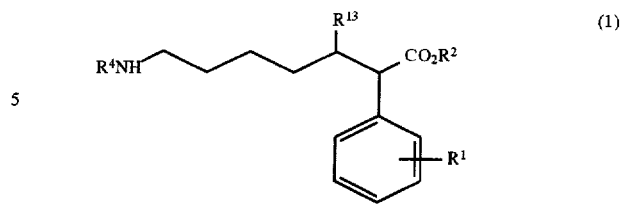

7-(N-substituted amino)-3-hydroxy-2-phenylheptanoate derivatives represented by the following formula (3):

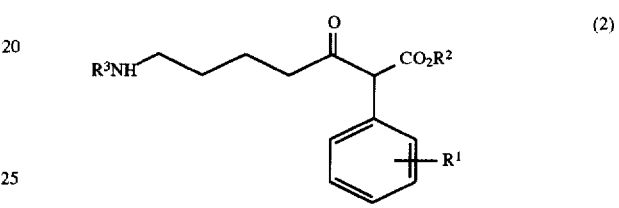

and 7-(N-substituted amino)-3-benzenesulfonyloxy-2-phenylheptanoate derivatives represented by the following formula (4):

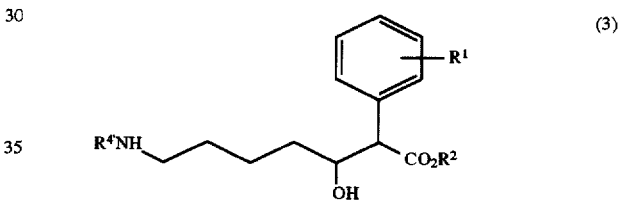

wherein $R^1$ and $R^2$ are the same groups as defined for formula (1); $R^3$ represents a hydrogen atom or a protective group for an amino group; $R^4$ represents a hydrogen atom or a protective group for an amino group; and $R^5$ represents a benzenesulfonyl group which may contain a substituted group.

DETAILED DESCRIPTION OF THE INVENTION

In the compounds represented by the above formulae, examples of the groups represented by $R^1$ include a methyl group, ethyl group, propyl group, and the like as the lower alkyl group and a methoxy group, ethoxy group, propoxy group, and the like as the lower alkoxy group. As examples of the lower alkyl groups represented by $R^2$ there are a methyl group, ethyl group, propyl group, and the like. Examples of the protective groups for the amino group represented by $R^3$ and $R^4$, include a benzyl group, benzyloxycarbonyl group, lower alkoxycarbonyl group having 1 to 4 carbon atoms, t-butyldimethylsilyl group, allyl group, and the like. The $R^1$ is substituted at para-cite preferably.

Examples of the substituted group of the benzenesulfonyl group include a lower alkyl group having 1 to 4 carbon atoms, such as a methyl group, ethyl group, and the like.

A preferred process for manufacturing the compound represented by formula (2) is as follows:

A 5-(N-substituted amino)pentanoic acid derivative represented by the following formula (6) is reacted with N,N'-carbonyldiimidazole (hereinafter abbreviated as "CDI") to prepare the imidazolide compound represented by the following formula (7):

wherein $R^3$ is the same groups as defined above;

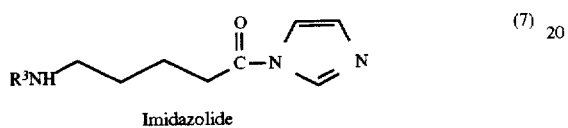

Imidazolide wherein $R^3$ is the same groups as defined above.

Next, the imidazolide compound of formula (7) is condensed with an enolate of phenylacetates represented by the following formula (6):

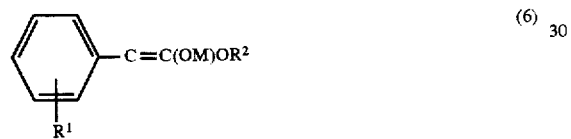

wherein M represents a lithium atom, and $R^1$ and $R^2$ are the same groups as defined above.

The imidazolide compound of formula (7) is preferably produced by the following method:

To the 5-(N-substituted amino)pentanoic acid derivative of formula (5) is added CDI in a proportion by molar equivalent of 1 to 1.5 based on the 5-(N-substituted amino) pentanoic acid derivative of formula (5) and the resulting mixture was stirred in tetrahydrofuran (hereinafter referred to as "THF") at 0° C. to room temperature for 2 to 30 hours.

To the imidazolide compound of formula (7) obtained in this manner is added the enolate of the phenylacetates represented of formula (6) in a proportion by molar equivalent of 1 to 1.5 per 1 mol of the imidazolide compound of formula (7) and the mixture is condensed at −70° to 0° C. for 1.5 to 4 hours to produce the 7-(N-substituted amino) -3-oxo-2-phenylheptanoic acid derivative represented of formula (2) in an efficient manner.

The derivative represented by formula (5) is a known compound and can be prepared, for example, by the following process:

Benzyloxycarbonyl chloride or di-t-butyl dicarbonate is added to a sodium hydroxide solution of 5-aminopentanoic acid which is commercially available. The mixture is stirred at room temperature for 18 hours, to which hydrochloric acid is added to adjust the pH to 3. The mixture is then extracted with ethyl acetate followed by purification using any conventional process.

The enolate of phenylacetates of formula (6) can be prepared by the following process:

Specifically, one of a phenylacetates and a lithium alkylamide are reacted at −70° to 0° C. in an ether type solvent or an aromatic hydrocarbon.

The novel compound of formula (3) can be prepared by the following process:

(a) by reacting a 7-(N-substituted amino)-3-oxo-2-phenylheptanoic acid derivative represented by formula (2) with hydrogen in the presence of a complex of a Group VIII transition metal including an optically active phosphine complex as a ligand; or (b) by reduction-reacting a 7-(N-substituted amino)-3-oxo-2-phenylheptanoic acid derivative represented by formula (2) with a chemical reducing agent.

A protective group for an amino group may be removed using any conventionally known method.

Because the novel compound represented by formula (3) has two asymmetrical carbons, it includes the four optical isomers shown in Table 1. Therefore, if the above process (a) is used, a product containing a specific optical isomer in a large amount can be prepared.

Table 1

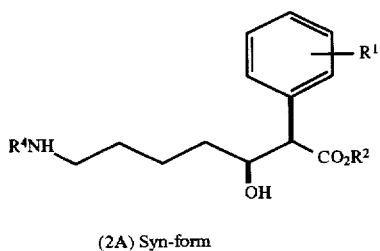

(2A) Syn-form

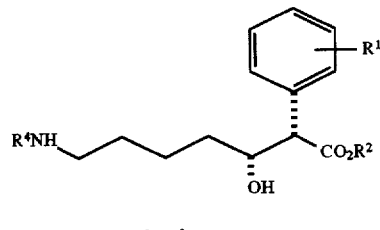

(2A) Syn-form

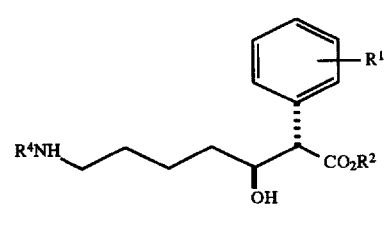

(2B) Anti-form

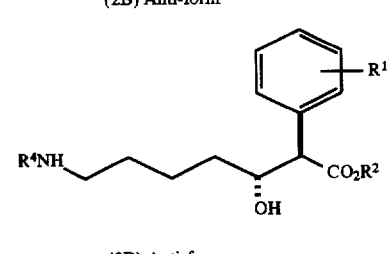

(2B) Anti-form wherein $R^1$, $R^2$ and $R^4$ are the same groups as defined above.

The complexes of the Group VIII transition metal used in the present invention include the compounds of the following formula (8):

wherein $M^1$ represents a ruthenium atom, iridium atom, or rhodium atom; L represents an optically active phosphine ligand; X represents a hydrogen atom, halogen atom or and carboxylic acid derivative residue; Q represents ethylene, 1,5-octadiene, benzene, p-cymene, mesitylene or the like; Y represents an anion selected from a group consisting of $ClO_4^-$, $BF_4^-$, and $PF_6^-$; m, n, and s respectively denote an integer of 1 or 2; r denotes an integer of 0 or 1; and q denotes an integer of from 0 to 2.

The ligand suitable for the optically active phosphine ligand used in the present invention is described below, though it maybe any optically active phosphine ligands known before the present patent application.

The carboxylic acid derivative residue is a group represented by the following formula (9):

wherein $R^6$ represents an alkyl group having 1–4 carbon atoms which may contain halogen atom. Preferred examples include a methyl group, trifluoromethyl group, tribromomethyl group or t-butyl group.

The complexes used in the present invention include the complexes having a coordinated group of the formula $NR^7R^8R^9$ furthermore coordinated, wherein $R^7$, $R^8$, and $R^9$ may be the same or different, and each represent a lower alkyl group having from 1 to 4 carbon atoms and two groups among $R^7$, $R^8$, and $R^9$ may form a hetrocyclic ring In combination with a nitrogen atom.

Preferred examples of the compound represented by the formula $NR^7R^8R^9$ are triethylamine, tributylamine, pyridine, ethyldiisopropylamine, 1,8-bis(dimethylamino) naphthalene, dimethylaniline,N-methylpiperidine, and the like.

The complexes used in the present invention include complexes obtained by adding a Lewis acid such as a metal halide to the above complexes with which the amine is coordinated, and agitating the resulting mixture.

Preferred examples of the metal halides include titanium tetrachloride, titanium tetrabromide, tin dichloride, iron trichloride, aluminum chloride, calcium chloride, samarium chloride, samarium iodide, lanthanum chloride, and cerium chloride.

Among the above complexes, particularly preferred are:

1) Complexes represented by the formula RuXY(L), wherein X represents a hydrogen atom, halogen atom or carboxylic acid derivative residue; Y represents a halogen atom or carboxylic acid derivative residue; and L represents an optically active phosphine ligand.

2) Complexes represented by the general formula [RuX (L)Q]Y, wherein X, Y, L are the same as above, Q represents ethylene, 1,5-octadiene, benzene, p-cymene, mesitylene or the like.

3) Complexes represented by the general formula [Ru₂Cl₄ (L)₂]NR⁷R⁸R⁹, wherein L, R⁷, R⁸ and R⁹ are the same as defined above.

4) Complexes represented by the general formula [IrQ(L) ]Y, wherein L and Q are the same as defined above.

5) Complexes represented by the general formula [RhQ (L)]Y, wherein Y, L, and Q are the same as defined above.

In this invention, the complex can be added to a reaction system to conduct a hydrogenating reaction. An alternative process may be employed in which components of the complex are mixed in advance or not mixed and then added to the reaction system to be hydrogenated.

Specifically, one molar equivalents of [iridium (cyclooctadienyl) chloride]₂ (hereinafter abbreviated as "[Ir (COD)Cl]₂") or [rhodium (cyclooctadienyl) chloride]₂ (hereinafter abbreviated as "[Rh(COD)Cl]₂"), two molar equivalents of optically active phosphine ligand, and a solvent are placed in an autoclave and agitated to prepare a complex.

Alternatively, a solvent such as methylene chloride or the like is added to the complex of the general formula [Ru₂Cl₄ (L)₂]NR⁶R⁷R⁸ in an amount from 5 to 10 times that of the complex to dissolve the complex. To the mixture is added from 1 to 5 molar equivalents of a metal halide, which is agitated at room temperature for 2 to 18 hours, followed by concentration under reduced pressure to prepare a complex.

As specific examples of the optically active phosphine ligand used in this process are (R)-2,2'-bis-(diphenylphosphino)-1,1'-binaphthyl (hereinafter abbreviated as "BINAP"), (R)-2,2'-bis-(di-p-tolylphosphino)-1,1'-binaphthyl (hereinafter abbreviated as "Tol-BINAP"), (R)-2,2'-bis-(di-p-chlorophenylphosphino)-1,1'-binaphthyl (hereinafter abbreviated as "p-Cl-BINAP"), 2,2'-bis (diphenylphosphino)-5,5',6,6',7,7',8,8'-octahydro-1,1'-binaphthyl (hereinafter abbreviated as "H8-BINAP"), (R)-2,2'-bis-(di-3,5-xylylphosphino)-1,1'-binaphthyl (hereinafter abbreviated as "DM-BINAP"), (R)-2,2'-bis (dicyclohexylphosphino)-6,6'-dimethyl-1,1'-biphenyl (hereinafter abbreviated as "BICHEP"), (R)-2,2'-bis-(diphenylphosphino)-6,6'-dimethyl-1,1'-biphenyl (hereinafter abbreviated as "BIPHEMP"), (+)-2,2'-bis (diphenylphosphino)-4,4',6,6'-tetramethyl-5,5'-dichloro-1, 1'-biphenyl (hereinafter abbreviated as "CM-BIPHEMP"), (R)-2-(dibiphenylphosphino)-2'-(diphenylphosphino)-1,1'-binaphthyl (hereinafter abbreviated as "Biph-Ph-BINAP"), and (R)-2-(dicyclohexylphosphino)-2'-(diphenylphosphino) -1,1'-binaphthyl (hereinafter abbreviated as "Cy-Ph-BINAP").

As the transition metal of these complexes, a rhodium atom, ruthenium atom, iridium atom, or the like are preferably used. Among these, the ruthenium atom or the iridium atom is more preferred.

More specific examples of the transition metal complex are shown in Table 2.

TABLE 2

RuXY (L)

RuCl₂(BINAP), RuCl₂(Tol-BINAP), RuCl₂(p-Cl-BINAP) RuCl₂(H8-BINAP), RuCl₂(DM—BINAP), RuCl₂(BICHEP), RuCl₂(BIHEMP), RuCl₂(CM—BIPHEMP), RuCl₂(BIPh-Ph-BINAP), RuCl₂(Cy-Ph-BINAP), RuBr₂(BINAP), RuBr₂(Tol-BINAP), RuBr₂(p-Cl-BINAP), RuBr₂(H8-BINAP), RuBr₂(DM—BINAP), RuBr₂(BICHEP), RuBr₂(BIPHEMP), RuBr₂(CM—BIPHEMP), RuBr₂(BIPh-Ph-BINAP), RuBr₂(Cy-Ph-BINAP), RuCl₂(BINAP), RuCl₂(Tol-BINAP), RuHCl(p-Cl-BINAP), RuHCl(H8-BINAP), RuHCl(DM—BINAP), RuHCl(BICHEP), RuHCl(BIPHEMP), RuHCl(CM—BIPHEMP), RuHCl(BIPh-Ph-BINAP), RuHCl(Cy-Ph-BINAP), Ru(OCOCH₃)₂(BINAP), Ru(OCOCH₃)₂(Tol-BINAP), Ru(OAc)₂(p-Cl-BINAP), Ru(OCOCH₃)₂(H8-BINAP), Ru(OCOCH₃)₂(DM—BINAP), Ru(OCOCH₃)₂(BICHEP), Ru(OCOCH₃)₂(BIPHEMP), Ru(OCOCH₃)₂(CM—BIPHEMP), Ru(OCOCH₃)₂(BIPh-Ph-BINAP), Ru(OCOCH₃)₂(Cy-Ph-BINAP), Ru(OCOCF₃)₂(BINAP), Ru(OCOCF₃)₂(Tol-BINAP), Ru(OCOCF₃)₂(p-Cl-BINAP), Ru(OCOCF₃)₂(H8-BINAP), Ru(OCOCF₃)₂(DM—BINAP), Ru(OCOCF₃)₂(BICHEP), Ru(OCOCF₃)₂(BIPHEMP), Ru(OCOCF₃)₂(CM—BIPHEMP), Ru(OCOCF₃)₂(BIPh-Ph-BINAP), Ru(OCOCF₃)₂(Cy-Ph-BINAP)

[RuX(L)Q]Y

[RuCl(benzene)(BINAP)]Cl, [RuCl(benzene)(Tol-BINAP)]Cl, [RuCl(benzene)(p-Cl-BINAP)]Cl, [RuCl(benzene)(H8-BINAP)]Cl, [RuCl(benzene)(DM—BINAP)]Cl, [RuCl(benzene)(BICHEP)]Cl, [RuClbenzene)(BIPHEMP)]Cl, [RuCl(benzene)(CM—BIPHEMP)]Cl, [RuCl(benzene)(BIPh-Ph-BINAP)]Cl, [RuCl(benzene)(Cy-Ph-BINAP)]Cl, [RuI(p-cymene)(BINAP)]I, [RuI(p-cymene)(Tol-BINAP)]I, [RuI(p-cymene)(p-Cl—BINAP)]I, [RuI(p-cymene)(H8-BINAP)]I, [RuI(p-

TABLE 2-continued cymene)(DM—BINAP)]I, [RuI(p-cymene)(BICHEP)]I, [RuI]p-
cymene)(BIPHEMP)]I [RuI(p-cymene)(CM—BIPHEMP)]I, [RuI(p-
cymene)(BIPh-Ph-BINAP)]I, [RuI(p-cymene)(Cy-Ph-BINAP)]I.
[Ru$_2$Cl$_4$(L)$_2$] NR$^5$R$^6$R$^7$ {Ru$_2$Cl$_4$(BINAP)$_2$}NEt$_3$, {Ru$_2$Cl$_4$(Tol-BINAP)$_2$}NEt$_3$, {Ru$_2$Cl$_4$(Cl-
BINAP)$_2$}NEt$_3$, {Ru$_2$Cl$_4$(H8-BINAP)$_2$}NEt$_3$, {Ru$_2$Cl$_4$(DM—
BINAP)$_2$}NEt$_3$, {Ru$_2$Cl$_4$(BICHEP)$_2$}NEt$_3$, {Ru$_2$Cl$_4$(BIPHEMP)$_2$}NEt$_3$,
{Ru$_2$Cl$_4$(CM—BIPHEMP)$_2$}NEt$_3$
[IrQ(L)]Y

[Ir(COD)(BINAP)]Cl, [Ir(COD)(Tol-BINAP)]Cl, [Ir(COD)(Cl-
BINAP)]Cl,[Ir(COD)(H8-BINAP)]Cl, [Ir(COD)(DM—
BINAP)]Cl, [Ir(COD)(BICHEP)]Cl, [Ir(COD)(BIPHEMP)]Cl, [Ir(COD)(C
M—BINAP)]Cl, [Ir(COD)(BIPh-Ph-BINAP)]Cl, [Ir(COD)(Cy-Ph-
BINAP)]Cl. [Ir(COD)(BINAP)]ClO$_4$, [Ir(COD)(Tol-BINAP)]ClO$_4$,
[Ir(COD)(BINAP)]BF$_4$, [IR(COD)(Tol-BINAP)]BF$_4$,
[Ir(COD)(BINAP)]PF$_6$, [Ir(COD)(Tol-BINAP)]PF$_6$
[RhQ(L)]Y

[Rh(COD)(BINAP)]Cl, [Rh(COD)(Tol-BINAP)]Cl, [Rh(COD)(Cl-
BINAP)]Cl, [Rh(COD)(H8-BINAP)]Cl, [Rh(COD)(DM—
BINAP)]Cl, [RH(COD)(BICHEP)]Cl,
[RH(COD)(BIPHEMP)]Cl, [Rh(COD)
(CM—BINAP)]Cl, [Rh(COD)(BIPh-Ph-BINAP)]Cl, [RH(COD)(Cy-Ph-
BINAP)]Cl, [Rh(COD)(BINAP)]ClO$_4$, [Rh(COD)(Tol-BINAP)]ClO$_4$,
[Rh(COD)(BINAP)]BF$_4$, [Rh(COD)(Tol-BINAP)]BF$_4$,
[Rh(COD)(BINAP)]PF$_6$, [Rh(COD)(Tol-BINAP)]PF$_6$

These transition metal complexes can be prepared according to known methods, for example, as disclosed in Japanese Patent Application Laid-open No. 61-265239 or Experimental Chemistry Lecture (Fourth edition), Vol. 18, Organic metal complex, Page 327–367.

In the present invention, the above transition metal complexes are used for a catalyst especially adapted for the assymetrical hydrogenation reaction. Furthermore this catalyst is used for assymetrical hydrogenation of the compound represented as the formula (2).

The above mentioned complexes are used in a molar amount of from 1/100 to 1/10,000 times, preferably from 1/200 to 1/1,000 times per one molar of the compound of the formula (2) or other compound to permit the asymmetrical hydrogenating reaction to proceed smoothly and to prepare an asymmetrically hydrogenated product with higher chemical purities and optical purities.

The assymetrical hydrogenating reaction is generally carried out at −30° C. to 250° C., preferably at 15° C. to 100° C., and under a hydrogen atmospher of from 1 to 200 atmospher, preferably from 10 to 100 atmospher.

The asymmetrical hydrogenation reaction is generally carried out in a solvent. Examples of the solvent include protic solvents such as methanol, ethanol, propanol, 2-propanol, and the like; and aprotic solvents such as methylene chloride, dichloroethane, tetrahydrofuran, dioxane, dimethoxyethane, dimethylformamide, dimethylsulfoxide, benzene, toluene, acetone, ethylacetate, and the like. These solvents may be used either alone or in combinations of two or more. In the present invention, methanol is most preferable as the solvent.

The solvent is designed to dissolve and contain the starting compound in a range from 1 to 50% by weight, preferably from 3 to 10% by weight based on the solvent weight.

In the present invention, an acid and/or metal halide are preferably added to the assymetric hydrogenating reaction system to promote the reaction rate and to improve asymmetric selectivity. Examples of the acid used include mineral acids such as hydrochloric acid, sulfuric acid, nitric acid, phosphoric acid, and the like; and organic acids such as organic carboxylic acids, organic sulfonic acids, and the like. Examples of the metal halide include titanium tetrachloride, titanium tetrabromide, tin dichloride, iron trichloride, aluminum chloride, calcium chloride, samarium chloride, samarium iodide, lanthanum chloride and cerium. These compounds may be used either alone or in combinations of two or more. The acid and metal halide may be used at the same time. Specifically, it is preferable to use D-camphor-10-sulfonic acid (hereinafter referred to as "D-CSA"), DL-camphor-10-sulfonic acid (hereinafter referred to as "DL-CSA"), 3-bromo-camphor-10-sulfonic acid (hereinafter referred to as "BSA"), or tin dichloride.

The acid and/or the metal halide may directly added to the reaction system, or may also be added to the reaction system after they are mixed with a solvent.

The proportion of the acid and/or the metal halide is from 1/10 to 5 mols, preferably from 0.7 to 1.2, based on the compound of formula (2).

The hydrogenated product may be directed to the next step, for example a step to manufacture the compound of formula (4), without any treatment. It is preferred that purified hydrogenation reaction product is applied in the next step to increase the content of a desired optically active compound.

Conventionally known processes may be employed for this purifying treatment.

An alternative process for manufacturing the above novel compound of formula (3) is illustrated below.

Specifically, the process for manufacturing the compound of formula (3) by reduction of 7-(N-substituted amino)-3-oxo-2-phenylheptanoic acid derivative represented of formula (2) using a chemical reducing agent is illustrated.

Examples of the reducing agent used include sodium borohydride, sodium trimethoxy borohydride, sodium cyanoborohydride, and the like. Among these, sodium borohydride is preferred from an economical point of view.

The proportion of the chemical reducing agent is preferred from 1 to 5 mols based on the compound of formula (2).

The reduction is usually carried out in lower alcohol having 1–4 carbon atoms,such as methanol, ethanol, isopropanol, or the like, preferably in methanol at temperatures ranging from −20° C. to 50° C., for 0.5 to 5 hours, adjusting the proportion of the compound of formula (2) of from 10 to 40% by weight.

After the reaction is terminated, for example, hydrochloric acid is added to the reaction solution to adjust the solution to an acidic condition, followed by extraction using ethylacetate to prepare the compound of the formula (3).

The 7-(N-substituted amino)-3-hydroxy-2-phenylheptanoic acid derivative of formula (3) is reacted with a benzenesulfonyl compound in a solvent containing a pyridine derivative to prepare the novel compound, specifically, 7-(N-substituted amino)-3-benzenesulfoniloxy-2-phenylheptanoic acid derivative represented by the following formula (4):

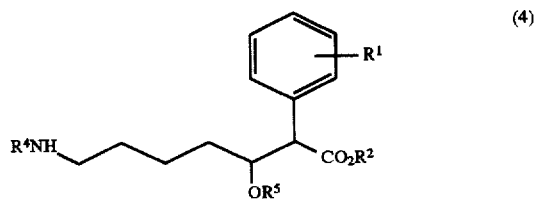

(4)

wherein R$^1$, R$^2$, R$^4$ and R$^5$ are the same groups as defined above.

This derivative includes two asymmetrical carbons. Therefore, four optical isomers similar to the optical isomers as shown in Table 1 exist.

Examples of the above benzenesulfonyl compound include benzenesulfonyl chloride, p-toluenesulfonyl chloride, m-toluenesulfonyl chloride, o-toluenesulfonyl chloride, and the like. Among these, p-toluenesulfonyl chloride is especially preferable. This benzenesulfonyl compound is formulated in a proportion by molar equivalent of 1 to 2 to the substrate.

Examples of the pyridine derivative include pyridine, bromopyridine, 3-methylpyridine, 2-methylpyridine, and the like.

As examples of the solvent preferably used in the present invention there are methylene chloride, dichloroethane, tetrahydrofuran, dioxane, dimethyloxyethane, dimethylformamide, dimethyl sulfoxide, pyridine, benzene, toluene, acetone, ethylacetate, and the like. In this case, if pyridine is used as the solvent, it is convenient because it serves as the above pyridine derivative.

This reaction is generally carried out at room temperature for 1 to 5 hours, adjusting the proportion of the substrate to 1 to 30% by weight.

If pyridine is used as the solvent, dimethylaminopyridine is allowed to coexist in a proportion of from 1/100 to 1/2 mols, preferably from 1/10 to 1/7 mols based on 1 mol of the compound of formula (3) to bring about desirable results, for example, to proceed the reaction smoothly.

After the reaction is completed, the reaction solution is acidified, for example, by adding hydrochloric acid and then extracted with a solvent such as ethylacetate to prepare the compound represented by the formula (4).

In addition, the protective group for the amino group may be removed using a known method as required.

The 7-(N-substituted amino)-3-benzenesulfonyloxy-2-phenylheptanoic acid derivative prepared in this manner is reacted with hydrogen in the presence of a catalyst to remove a protective group and is then cyclized in the presence of a base to prepare a 2-phenyl-2-(2'-piperidyl) acetate derivative represented by the following formula (10):

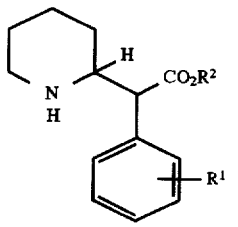

(10)

wherein $R^1$ and $R^2$ are the same as above-defined.

When the protective group-removing reaction and cyclization are performed using especially a compound containing the 7-(N-substituted amino)-3-benzenesulfonyloxy-2-phenylheptanoic acid derivative represented by following formula (11) in a large amount as a starting material, a product containing a large amount of the 2-phenyl-2-(2'-piperidinyl)acetate derivative represented by the following formula (12) can be obtained (refer to the method of the reference example):

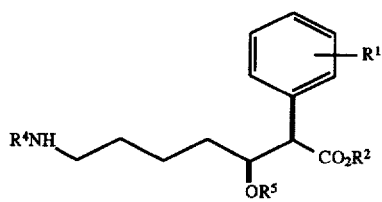

(11)

wherein $R^1$, $R^2$, $R^4$, $R^5$ are the same as above-defined;

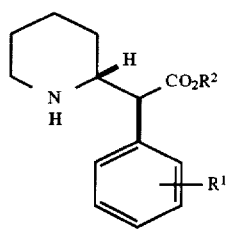

(12)

wherein $R^1$ and $R^2$ are the same as above-defined.

This 2-phenyl-2-(2'-piperidinyl)acetate derivative is epimerized in a known process to prepare the above antidepressant with ease.

EXAMPLES

The present invention will be illustrated in more detail by way of examples, which, however, shall not be construed as limiting the invention.

Example 1

Synthesis of methyl 7-(N-benzyloxycarbonylamino)-3-oxo-2-phenylheptanoate 70 g (279 mmol) of 5-(N-benzyloxycarbonylamino) pentanoic acid was dissolved in 350 ml of THF in a flask. 49.7 g (306 mmol) of CDI was dividedly added to the mixture in several times, which was then stirred at room temperature for 18 hours to synthesize an imidazolide compound.

109.5 ml (836 mmol) of diisopropylamine and 350 ml of THF were placed in another flask and cooled to −35° C. in a dry ice-acetone bath. Maintaining the temperature at −35° C., 513 ml (836 mmol) of 1.63N n-butyllithium (hexane solution) (hereinafter referred to as "BA solution") was added dropwise to the mixture for one hour. After the addition was completed, stirring was further continued at a same temperature for one hour to prepare lithium diisopropylamide. Then, 125.5 g (836 mmol) of methyl phenylacetate dissolved in 350 ml of THF was added dropwise to the lithium diisopropylamide for 45 minutes. After the addition, the resulting mixed solution was stirred at a same temperature for one hour to synthesize an enolate compound of methyl phenylacetate.

The above synthesized imidazolide compound was added dropwise to the enolate compound for one hour, maintaining the temperature constant. After the addition, the mixture was stirred for three hours. After the presence of the product was confirmed, 280 ml of saturated aqueous ammonium chloride solution was added to the mixture and then the reaction was terminated. 520 g of 4N hydrochloric acid was added to the reaction mixture to adjust the pH to 3, 1.4 of ethyl acetate was added to the mixture to separate an organic layer. To the organic layer was added 140 ml of a saturated sodium bicarbonate solution to neutralize. The neutralized organic layer was washed with saturated brine and then deied with magnesium sulfate anhydride. After the dried organic layer was concentrated under reduced pressure, the residue was purified by means of silica gel column chromatography (hereinafter referred to as "SGIC")(eluent: hexane/ethylacetate) to obtain the target compound as a pale yellow oil in an amount 71.1 g at a yield of 66.4%. The above reactional operations were all conducted under a nitrogen atmosphere. The analytical results on the target compound are given below.

¹H-NMR (CDCl₃/Me₄Si) δ: 1.40(m, 2H), 1.53 (m, 2H), 2.13 (m, 0.35H), 2.49 (m, 1.65H), 3.10(m, 1.86H), 3.19 (m, 0.14H), 3.67(s, 0.68H), 3.7 3(s, 2.32H), 4.70(s, 1.07H), 4.98(br, 1H), 5.07(s, 2H), 7.1–7.4(m, 5H), 1 3.1(s, 0.14H)

¹³C-NMR (CDCl₃) δ: 20.50, 21.96, 23.67, 29.03, 29.33, 32.15, 33.52, 40.43, 40.61, 40.91, 51.56, 51.88, 52.58, 64.82, 66.59, 127.23, 128.08, 123.23, 128.34, 128.43, 128.54, 128.92, 129.04, 129.32, 129.40, 131.23, 132.46, 134.81, 136.63, 156.39, 168.98, 173.12, 176.36, 203.33

Mass m/z: 384 (M+), 322; 308, 276, 244, 222, 190, 158, 108, 91

Analytic condition for the ratio of the syn-form to the anti-form:

High performance liquid chromatography(HPLC)
Column: Inertsil ODS-2 (manufactured by GL Science Co., Ltd.)
Eluent: Acetonitrile/water=7/3 by volume
Flow rate: 0.5 ml/min
Detector: UV=254 nm

Example 2

Synthesis of ethyl 7-(N-benzyloxycarbonylamino)-3-oxo-2-phenylheptanoate

The target compound was prepared as a pale yellow oil in an amount 3.8 g at a yield of 42.6% in the same manner as in Example 1 except that 5.7 g (22 mmol) of 5-(N-benzyloxycarbonylamino)pentanoic acid was dissolved in 23 ml of THF and 5.35 g (33 mmol) of CDI was dividedly added several times; 5.8 ml (44 mmol) of diisopropylamine and 10 ml of THF were added and 27.5 ml (44 mmol) of 1.63N BA solution was added dropwise; 6.6 ml (44 mmol) of ethyl phenylacetate instead of methyl phenylacetate was dissolved in 10 ml of THF; and 30 ml of saturated aqueous ammonium chloride solution was added to the reaction solution, the reaction was terminated, 50 g of 4N hydrochloric acid was added, and 100 ml of ethyl acetate was further added. The analytical results on the target compound are given below.

¹H-NMR (CDCl₃/Me₄Si) δ: 1.25, 1.26(dt, J=7 Hz, J=2.2 Hz, 3H), 1.3–1.9 (m, 4H), 2.32(t, J=6.8 Hz, 0.6H), 2.50(t, J=6.8 Hz, 1.4H), 3.0–3.3(m, 2H), 4.15(m, 2H), 4.68(s, 0.58H), 4.80(br, 1H), 5.08(s, 2H), 7.0–7.5(m, 10H)

Example 3

Synthesis of methyl 7-(N-benzyloxycarbonylamino)-3-oxo-2-p-tolylheptanoate

The target compound was prepared as a pale yellow oil in an amount 12.9 g at a yield of 67.9% in the same manner as in Example 1 except that 12 g (47.8 mmol) of 5-(N-benzyloxycarbonylamino)pentanoic acid was dissolved in 60 ml of THF and 8.41 g (52.5 mmol) of CDI was added; 14.5 g (143 mmol) of diisopropylamine and 60 ml of THF were added and 89.5 ml (143 mmol) of 1.63N BA solution was added dropwise; 23.5 ml (143 mmol) of methyl p-tolylacetate instead of methyl phenylacetate was dissolved in 60 ml of THF; and 48 ml of saturated aqueous ammonium chloride solution was added to the reaction solution, the reaction was terminated, 100 g of 4N hydrochloric acid was added, and 240 ml of ethyl acetate was further added. The analytical results on the target compound are given below.

¹H-NMR (CDCl₃/Me₄Si) δ: 1.42 (m, 2H), 1.56 (m, 2H), 2.12 (m, 0.3 3H), 2.34, 2.35(s, 3H), 2.49(m, 1.67H), 3.0–3.22(m, 2H), 3.68(m, 0.7H), 3.73(m, 2.3H), 4.66(s, 0.91H), 4.75(br, 0.63H), 5.07(s, 2H), 6.9–7.4(m, 9H)

¹³C-NMR (CDCl₃) δ: 20.52, 21.11, 29.06, 32.13, 40.56, 40.78, 51.87, 52.53, 64.51, 66.61, 128.08, 128.51, 129.00, 129.20, 129.47, 129.64, 131.04, 136.63, 138.20, 156.36, 169.14, 203.52

Mass m/z: 398(M+), 381, 366, 354, 336, 290, 266, 222, 190, 158, 108, 91

Example 4

Synthesis of methyl 7-(N-benzyloxycarbonylamino)-3-oxo- 2-p-methoxyphenylheptanoate The target compound was prepared as a pale yellow oil in an amount 6.3 g at a yield of 33.6% in the same manner as in Example 1 except that 11.6 g (46.2 mmol) of 5-(N-benzyloxycarbonylamino)pentanoic acid was dissolved in 50 ml of THF and 8.25 g (50.8 mmol) of CDI was added; 39.2 ml (277 mmol) of diisopropylamine and 60 ml of THF were added and 170 ml (277 mmol) of 1.63N BA solution was added dropwise; 25 g (139 mmol) of methyl p-methoxyacetate instead of methyl phenylacetate was dissolved in 50 ml of THF; and 50 ml of saturated aqueous ammonium chloride solution was added to the reaction solution, the reaction was terminated, 100 g of 4N hydrochloric acid was added, and 200 ml of ethyl acetate was further added. The analytical results on the target compound are given below.

¹H-NMR (CDCl₃/Me₄Si) δ: 1.24 (m, 2H), 1.40(m, 2H), 2.12(m, 0.35H), 2.49(m, 1.65H), 3.09 (m, 3H), 3.67(s, 0.58H), 3.72(s, 2.42H), 3.78, 3.80 (m, 3H), 4.65(s, 0.88H), 4.85(br, 0.86H), 5.06(s 2H), 6.8–7.4(m, 9H)

¹³C-NMR (CDCl₃) δ: 20.52, 21.03, 23.71, 29.06, 29.36, 32.17, 40.54, 40.79, 51.88, 52.52, 55.17, 55.28, 60.39, 63.95, 66.57, 113.69, 114.35, 124.50, 126.94, 128.51, 130.50, 132.24, 136.66, 156.40, 158.69, 159.61, 169.28, 173.36, 176.49, 203.68

Mass m/z: 413(M+), 380, 354, 337, 305, 272, 233, 279, 121, 108, 91

Example 5

Synthesis of t-butyl 7-(N-benzyloxycarbonylamino)-3-oxo- 2-phenylheptanoate

The target compound was prepared as a colorless solid substance in an amount 5.94 g at a yield of 70.2% in the same manner as in Example 1 except that 5.0 g (19.9 mmol) of 5-(N-benzyloxycarbonylamino)pentanoic acid was dissolved in 50 ml of THF and 3.55 g (21.9 mmol) of CDI was added; 7.83 ml (59.7 mmol) of diisopropylamine and 30 ml of THF were added and 37 ml (59.7 mmol) of 1.63N BA solution was added dropwise; 11.5 g (59.7 mmol) of t-butyl phenylacetate instead of methyl phenylacetate was dissolved in 30 ml of THF; and 50 ml of saturated aqueous ammonium chloride solution was added to the reaction solution, the reaction was terminated, 40 g of 4N hydrochloric acid was added, and 140 ml of ethyl acetate was further added. The analytical results on the target compound are given below.

m.p.: 74° C.–76° C.

¹H-NMR (CDCl₃/Me₄Si) δ: 1.41(m, 2H), 1.46(s, 9H), 1.59(m, 2H), 2.1 5(m, 0.12H), 2.45(m, 1.88H), 3.12(m, 2H), 4.61(s, 2H), 4.76(br, 0.83H); 5.08(s, 2H), 7.28–7.4(m, 5H),

¹³C-NMR (CDCl₃) δ: 20.54, 27.95, 29.10, 40.58, 40.97, 65.89, 128.08, 128.51, 128.76, 129.38, 132.96, 136.63, 156.36, 167.62, 203.80

Mass m/z: 426(M+), 370, 352, 326, 308, 234, 218, 190, 131, 118, 91

Example 6

Synthesis of methyl 7-(N-t-butoxycarbonylamino)-3-oxo-2-phenylheptanoate

The target compound was prepared as a pale yellow oil in an amount 7.7 g at a yield of 95.7% in the same manner as in Example 1 except that 5.0 g (23 mmol) of 5-(N-t-butoxycarbonylamino)pentanoic acid instead of 5-(N-benzyloxycarbonylamino)pentanoic acid was dissolved in 25 ml of THF and 4.1 g (25.3 mmol) of CDI was added; 9.05 ml (69 mmol) of diisopropylamine and 25 ml of THF were added and 42 ml (69 mmol) of 1.63N BA solution was added dropwise; 10.4 g (69 mmol) of methyl phenylacetate was dissolved in 25 ml of THF; and 30 ml of saturated aqueous ammonium chloride solution was added to the reaction solution, the reaction was terminated, 50 g of 4N hydrochloric acid was added, and 100 ml of ethyl acetate was further added. The analytical results on the target compound are given below.

$^1$H-NMR (CDCl$_3$/Me$_4$Si) δ: 1.40(m, 2H), 1.43(s, 9H), 1.57(m, 2H), 2. 11(t, J=7.1 Hz, 0.47H), 2.50(t, J=7.1 Hz, 1.53), 3.03(m, 2H), 3.68(s, 0.75H), 3.74(s, 2.25H), 3.35–3.6 (br, 1H), 7.1–7.45(m, 5H), 13.05(s, 0.2H)

$^{13}$C-NMR (CDCl$_3$) δ: 20.61, 29.16, 29.46, 32.23, 51.86, 52.57, 64.82, 127.21, 128.32, 128.90, 128.94, 129.37, 131.24, 132.47, 134.84, 155.94, 168.97, 173.13, 176.49, 203.34

Mass m/z: 350(M+), 294, 276, 262, 250, 232, 217, 199, 172, 14 3, 118, 100, 89

Example 7

Synthesis of ethyl 7-(N-t-butoxycarbonylamino)-3-oxo-2-phenylheptanoate

The target compound was prepared as a pale yellow oil in an amount 7.8 g at a yield of 48.1% in the same manner as in Example 1 except that 10 g (45.8 mmol) of 5-(N-t-butoxycarbonylamino)pentanoic acid instead of 5-(N-benzyloxycarbonylamino)pentanoic acid was dissolved in 70 ml of THF and 11.1 g (68.7 mmol) of CDI was added; 9.5 ml (72 mmol) of diisopropylamine and 40 ml of THF were added and 42 ml (69 mmol) of 1.63N BA solution was added dropwise; 10.6 g (68.7 mmol) of ethyl phenylacetate instead of methyl phenylacetate was dissolved in 20 ml of THF; and 30 ml of saturated aqueous ammonium chloride solution was added to the reaction solution, the reaction was terminated, 70 g of 4N hydrochloric acid was added, and 100 ml of ethylacetate was further added. The analytical results on the target compound are given below.

$^1$H-NMR (CDCl$_3$/Me$_4$Si) δ: 1.26(dt, J=7.2 Hz, J=2.5 Hz, 3H), 1.40(m, 2H), 1.42(s, 9H), 1.55 (m, 2H), 2.11 (t, J=7.5 Hz, 0.37H), 2.50(t, J=7.1 Hz, 1.63H), 3.05(m, 2H), 4.22(dq, J=7.2 Hz, J=2.5 Hz, 2H), 4.50(br, 0.79H), 4.70(s, 0.78H), 7.1–7.4(m, 5H)

hu 13C-NMR (CDCl$_3$) δ: 14.07, 14.23, 20.62, 22.10, 28.41, 33.87, 40.98, 61.61, 65.00, 128.25, 128.86, 129.37, 131.25, 132.61, 155.93

Mass m/z: 364(M+), 308, 290, 278, 264, 218, 200, 164, 144, 118, 100, 89

Example 8

Synthesis of methyl 7-(N-benzyloxycarbonylamino)-3-hydroxy-2-phenylheptanoate 22.6 g (58.8 mmol) of methyl 7-(N-benzyloxycarbonylamino)- 3-oxo-2-phenylheptanoate, 435 mg (0.39 mmol) of [RuI(p-cymene)(S)-BINAP]I, 72 mg (0.39 mmol) of tin chloride and 364 mg (1.56 mol) of camphor-10-sulfonic acid (hereinafter referred to as "CSA") were placed in a 500 ml autoclave. After air in the autoclave was replaced with nitrogen, 160 ml of methanol was added to the mixture. The nitrogen in the autoclave was replaced with hydrogen and then the mixed solution was reacted at 80° C. under a hydrogen pressure of 80 kg/cm$^2$ for 40 hours. After the completion of the reaction was confirmed by means of HPLC, the reaction solution was concentrated under reduced pressure. The residue was then purified by means of SGIC (eluent: hexane/ethylacetate=2/1 by volume) to prepare the target compound as a colorless oil in an amount of 37.4 g at a yield of 87.4%. The products were analyzed using HPLC. As a result, the rate of the syn-form to the anti-form was 76.3:23.7 and the optical purity of each of the forms was 95.6% ee and 97.8% ee respectively. The analytical results on the target compound are given below.

Syn-form m.p.: 62° C.–64° C.

$^1$H-NMR (CDCl$_3$/Me$_4$Si) δ: 1.3–1.85(m 6H), 2.44(br, 1H), 3.17(m, 2H), 3.56(d, J=6.5 Hz, 1H), 3.66(s, 3H), 4.17 (m, 1H), 4.80(m, 1H), 5.08(br, 1H), 7.35(m, 9H)

$^{13}$C-NMR (CDCl$_3$/Me$_4$Si) δ: 22.88, 29.73, 33.99, 40.88, 52.12, 57.27, 66.58, 71.99, 127.85, 128.06, 128.10, 128.50, 128.73, 129.19, 135.01, 136.67, 156.67, 173.66

Mass m/z: 386(M+), 342, 324, 278, 234, 218, 192, 174, 151, 108, 91, 79

Anti-form $^1$H-NMR (CDCl$_3$/Me$_4$Si) δ: 1.2–1.6(m, 6H), 2.87(d, J=4.9 Hz, 1H), 3.11(m 2H), 3.56(d, J9.1 Hz, 1H), 3.68(s, 3H), 4.12(m, 1H), 4.72(br, 1H), 5.08(s, 2H), 7.18–7.40(m, 9H)

$^{13}$C-NMR (CDCl$_3$/Me$_4$Si) δ:22.48, 29.69, 33.29, 40.83, 52.19, 58.59, 66.60, 73.07, 127.75, 128.08, 128.32, 128.51, 128.91, 136.05, 138.64, 156.40, 174.11

Mass m/z: 386(M+), 342, 324, 278, 234, 218, 192, 174, 151, 118, 107, 91, 79

Analytical condition of the optical purity of the product:

High performance liquid chromatography(HPLC)

Column: Ceramospher Chiral Ru-1 (manufactured by Shiseido Co., Ltd.)

Eluent: Methanol

Flow rate: 0.15 ml/min

Detector UV=254 nm

Example 9

Synthesis of ethyl 7-(N-benzyloxycarbonylamino)-3-hydroxy-2-phenylheptanoate The same procedures as in Example 8 were performed except that 0.1 g (0.25 mmol) of ethyl 7-(N-benzyloxycarbonylamino)-3-oxo-2-phenylheptanoate and 1.4 mg (0.00125 mmol) of [RuI(p-cymene)(S)-BINAP]I were placed in an 100 ml autoclave, 2 ml of methanol was added, and the reaction was performed under a hydrogen pressure of 65 kg/cm$^2$ for 18 hours, to prepare the target compound as a colorless oil. (Yield was 65.3%) The ratio of the syn-form to the anti-form was 87.5:12.5, and the optical purity of the syn-form was 93.2% ee.

Example 10–13

Synthesis of ethyl 7-(N-benzyloxycarbonylamino)-3-hydroxy-2-phenylheptanoate The same procedures as in Example 9 were performed except that the complexes and the solvents were changed to those given in Table 4, the hydrogen pressure was changed to 65 kg/cm$^2$, and the reaction time was changed to 18 hours. The results are shown in Table 4.

TABLE 4

| Example | Solvent | Complex | Yield | Syn:Anti |
|---|---|---|---|---|
| 10 | Ethanol | [RuI(p-cymene)((S)-p-Cl-binap)]I | 82.8 | 71.1(65.1% ee):28.9 |
| 11 | Ethanol | {Ru₂Cl₄((R)-p-Cl-binap)₂}NEt₃ | 77.0 | 48.3(44.5% ee):51.7 |
| 12 | Ethanol | [RuI(p-cymene)((S)-binap)]I₃ | 97.1 | 65.5(77.6% ee):34.5 |
| 13 | Methylene chloride-Methanol | [RuI(p-cymene)((S)-binap)]I | 74.3 | 80.2(92.8% ee):19.8 |

Example 14

Synthesis of ethyl 7-(N-benzyloxycarbonylamino)-3-hydroxy-2-phenylheptanoate

The same procedures as in Example 9 were performed except that BSA was added to the reaction system in an amount of 8.2 mg (0.025 mol). The yield of the product was 93.2% and the ratio of the syn-form to the anti-form was 71.0:29.0. Also, The optical purity of the syn-form was also 80.0% ee.

Example 15–18

Synthesis of ethyl 7-(N-benzyloxycarbonylamino)-3-hydroxy-2-phenylheptanoate

The same procedures as in Example 5 were performed except that the additives given in Table 5 were used instead of BSA. The results are shown in Table 5.

TABLE 5

| Example | Additive | Yield | Syn:Anti |
|---|---|---|---|
| 15 | SnCl₂ | 38.4 | 79.0(90.0% ee):21.0 |
| 16 | SnCl₂ + BSA | 100 | 97.2(72.4% ee):2.8 |
| 17 | SnCl₂ + D-CSA | 34.3 | 80.0(90.0% ee):19.7 |
| 18 | SnCl₂ + DL-CSA | 75.3 | 80.0(89.1% ee):20.0 |

(SnCl₂ 0.3 mg, BSA 8.2 mg, D-CSA 1.2 mg, DL-CSA 1.2 mg)

Example 19–24

Synthesis of ethyl 7-(N-benzyloxycarbonylamino)-3-hydroxy-2-phenylheptanoate

The same procedures as in Example 14 were performed except that the catalysts given in Table 6 were used instead of [RuI(p-cymene)(S)-BINAP]I, and 8.2 mg of BSA or a combination of 10.3 mg of tin chloride and 8.2 mg of BSA was used as an additive. The results are shown in table 6.

Example 25

Synthesis of ethyl 7-(N-t-butoxycarbonylamino)-3-hydroxy-2-phenylheptanoate

The same procedures as in Example 14 were performed except that 0.1 g (0.28 mmol) of ethyl 7-(N-t-butoxycarbonylamino)-3-oxo-2-phenylheptanoate, 6.2 mg (0.0056 mmol) of [RuI(p-cymene)(S)-BINAP]I, 9.2 g (0.028 mol) of BSA, and 2 ml of methanol were used. The yield of the product was 65.3% and the ratio of the syn-form to the anti-form was 56.5:43.5.

Example 26

Synthesis of ethyl 7-(N-benzyloxycarbonylamino)-3-hydroxy-2-phenylheptanoate 6 g (14.1 mmol) of 7-(N-benzyloxycarbonylamino)-3-oxo-2-phenylheptanoic acid was dissolved in 30 ml of methanol. The mixture was cooled in an ice bath. 533 mg (14.1 mol) of sodium borohydride was dividedly added to the mixture several times, which was then stirred at a same temperature. After the consumption of the raw material was confirmed by means of HPLC, 10 ml of 4N hydrochloric acid was added to the reaction mixture to adjust the pH to 3. Ethylacetate was added to the mixture to separate an organic layer. To the organic layer was added a saturated sodium bicarbonate to neutralize. The neutralized organic layer was washed with saturated brine and then deied with magnesium sulfate anhydride. After the dried organic layer was concentrated under reduced pressure, the residue was purified by means of SGIC (eluent: hexane/ethylacetate=2/1 by volume) to obtain the target compound as a colorless oil in an amount 2.53 g at a yield of 42.0%. The products were analyzed by means of HPLC. As a result, the ratio of the syn-form to the anti-form was 70.4:29.6. The analytical results on the target compound are given below.

Syn-form

¹H-NMR (CDCl₃/Me₄Si) δ: 1.20, 1.26(dt, J=19.9 Hz, J=7.1 Hz, 3H), 1.3–1.65(m, 6H), 2.43(s, 1H), 3.18(m, 2H), 3.54(d, J=6 Hz, 1H), 4.09, 4.16(dq, J=7.1 Hz, J=19.9 Hz, 2H), 4.13(m, 1H), 4.76(br, 0.86H), 5.09(s, 2H), 7.34(m, 9H)

TABLE 6

| Example | Complex | Additive | Yield | Syn:Anti |
|---|---|---|---|---|
| 19 | [RuI(p-cymene)(R)-biphemp]I | SnCl₂ + BSA | 95.7 | 62.4(88.3% ee):37.6 |
| 20 | {Ru₂Cl₄((R)-binap)₂}NEt₃ | SnCl₂ + BSA | 44.5 | 78.2(92.3% ee):21.8 |
| 21 | [RuI(p-cymene)((R)-tol-binap)]I | SnCl₂ + BSA | 100 | 81.7(93.8% ee):18.3 |
| 22 | [RuI(p-cymene)((s)-DM-binap)]I | SnCl₂ + BSA | 66.8 | 66.2(93.6% ee):33.8 |
| 23 | [RuI(p-cymene)((R)-H8-binap)]I | BSA | 100 | 66.3(90.1% ee):33.7 |
| 24 | [RuI(p-cymene)((R)-binap)]I₃ | BSA | 90.4 | 65.5(77.6% ee):34.5 |

[SnCl₂ 10.3 mg, BSA 8.2 mg]

$^{13}$C-NMR (CDCl$_3$/Me$_4$Si) δ: 14.05, 21.04, 22.90, 29.76, 33.97, 40.91, 57.37, 61.03, 66.60, 72.02, 127.80, 128.07, 128.51, 128.70, 129.19, 135.08, 136.67, 173.24

Mass m/z: 400(M+), 356, 310, 292, 248, 192, 164, 118, 100

Anti-form $^1$H-NMR (CDCl$_3$/Me$_4$Si) δ: 1.17(t, J=7.2 Hz, 3H), 1.2–1.6(m, 6H), 2.90(d, 5 Hz, 1H), 3.11(m, 2H), 3.54(d, 9.1 Hz, 1H), 4.12, 4.19(t, J=7.2 Hz, 2H), 4.13(m, 1H), 4.73(br, 1H), 5.07(s, 2H), 7.2–7.4(m, 9H)

$^{13}$C-NMR (CDCl$_3$/Me$_4$Si) δ: 14.04, 22.52, 22.90, 29.70, 33.36, 40.85, 58.71, 61.09, 66.60, 73.15, 127.66, 127.79, 128.08, 128.11, 128.32, 128.51, 128.70, 128.85, 129.19, 136.22, 135.66, 156.41, 173.66

Mass m/z: 400(M+), 356, 310, 292, 248, 218, 192, 164, 118, 91

Example 27

Synthesis of methyl 7-(N-t-butoxycarbonylamino)-3-hydroxy-2-phenylheptanoate

The same procedures as in Example 26 were performed except that 1 g (2.75 mmol) of methyl 7-(N-t-butoxycarbonylamino)-3-oxo-2-phenylheptanoate instead of ethyl 7-(N-t-butoxycarbonylamino)-3-oxo-2-phenylheptanoate was dissolved in 6 ml of methanol, 104 mg (2.75 mol) of sodium borohydride was added, and 5 ml of 4N hydrochloric acid was added to the reaction solution, to prepare the target compound as a pale yellow oil in an amount of 0.9 g at a yield of 90.0%. The products were analyzed to result in that the ratio of the syn-form to the anti-form was 9:1. The analytical results on the target compound are given below.

Syn-form $^1$H-NMR (CDCl$_3$/Me$_4$Si) δ: 1.20(t, J=7.1 Hz, 3H), 1.43(s, 9H), 1.3–1.69m, 6H), 2.50(s, 1h), 3.09(m, 2H), 3.55(d, J=6.4 Hz, 1H), 4.11, 4.16(q, J =7.1H, 2H), 4.15(m, 1H), 4.56(br, 1H), 7.33(m, 9H)

$^{13}$C-NMR (CDCl$_3$/Me$_4$Si) δ: 14.02, 22.54, 28.42, 29.80, 33.45, 58.77, 60.97, 72.05, 73.14, 127.61, 127.71, 128.33, 128.62, 128.79, 129.18, 136.25, 156.02, 173.63

Mass m/z: 366(M+), 310, 292, 266, 248, 164, 146, 118, 102, 84

Anti-form $^1$H-NMR (CDCl$_3$/Me$_4$Si) δ: 1.19(t, J=7.1 Hz, 3H), 1.2–1.7(m, 6H), 3.0 5(m, 2H), 3.55(d, J=9.1 Hz, 1H), 4.12, 4.17(q, J=7.1 Hz, 2H), 4.13(m, 1H), 4.58(br, 1H), 7.2–7.4 (m, 9H)

$^{13}$C-NMR (CDCl$_3$/Me$_4$Si) δ: 13.99, 22.88, 28.40, 29.77, 34.18, 40.33, 57.58, 60.86, 72.01, 78.84, 127.57, 128.50, 129.14, 135.45, 156.06, 173.10

Mass m/z: 366(M+), 310, 292, 266, 248, 164, 146, 118, 102, 91

Example 28

Synthesis of methyl 7-(N-benzyloxycarbonylamino)-3-hydroxy-2-phenylheptanoate

The same procedures as in Example 26 were performed except that 987 mg (26.1 mol) of sodium borohydride was added and 15 ml of 4N hydrochloric acid was added to the reaction solution, to prepare the target compound as a pale yellow oil in an amount of 5.80 g at a yield of 57.6%. The products were analyzed to result in that the ratio of the syn-form to the anti-form was 87.6:12.3.

Example 29

Synthesis of t-butyl 7-(N-benzyloxycarbonylamino)-3-hydroxy-2-phenylheptanoate

The same procedures as in Example 26 were performed except that 0.2 g (0.47 mmol) of t-butyl 7-(N-benzyloxycarbonylamino)-3-oxo-2-phenylheptanoate instead of ethyl 7-(N-benzyloxycarbonylamino)-3-oxo-2-phenylheptanoate was dissolved in 4 ml of methanol, 18 mg (0.47 mol) of sodium borohydride was added, and 4 ml of 4N hydrochloric acid was added to the reaction solution, to prepare the target compound as a pale yellow oil in an amount of 196 mg at a yield of 98%. The selectivity of the products in terms of the ratio of the syn-form to the anti-form was 7:3. The analytical results on the target compound are given below.

$^1$H-NMR (CDCl$_3$/Me$_4$Si) δ: 1.2–1.7(m, 6H), 1.38, 1.39(s, 9H), 2.50, 2.98(d, J=2.3 Hz, J=5 Hz, 1H), 3.08–3.2(m, 3H), 3.44, 3.45(d, J=8.3 Hz, J=6.5 Hz, 1H), 4.09(m, 1H), 4.77(m, 1H), 5.07, 5.09(s, 2H), 7.31(m, 9H)

$^{13}$C-NMR (CDCl$_3$/Me$_4$Si) δ: 22.59, 22.92, 27.93, 29.80, 33.46, 33.96, 40.95, 58.15, 59.34, 60.39, 66.58, 72.03, 73.22, 81.47, 81.54, 127.40, 127.57, 128.06, 128.11, 128.22, 128.51, 128.57, 128.70, 129.12, 135.48, 136.68, 136.76, 156.40, 172.59, 173.00

Mass m/z: 428(M+), 372, 354, 328, 310, 264, 236, 218, 192, 136, 118, 91, 77

Example 30

Synthesis of ethyl 7-(N-benzyloxycarbonylamino)-3-p-toluenesulfonyloxy-2-phenylheptanoate 3.5 g (8.6 mmol) of ethyl 7-(N-benzyloxycarbonylamino)-3-hydroxy-2-phenylheptanoate obtained in Example 9 was dissolved in 28 ml of pyridine. 240 mg (1.96 mmol) of dimethylaminopyridine was added to the mixture. The mixture was cooled at 0° C. in an ice bath. 2.5 g (13 mmol) of p-toluenesulfonyl chloride was added for 5 minutes, which was stirred for one hour at a same temperature and further stirred at room temperature for 48 hours. After the consumption of the raw material was confirmed by means of HPLC, 100 ml of ethylacetate was added and 2N hydrochloric acid were further added to the reaction mixture to adjust the pH to 4 to extract. A saturated sodium bicarbonate solution was added to the organic layer prepared to neutralize. The neutralized organic layer was washed with saturated brine and then deied with magnesium sulfate anhydride. After the organic layer was concentrated under reduced pressure, the residue was purified by means of SGIC (eluent: hexane/ethylacetate=3/1) to obtain the target compound as a pale yellow oil in an amount 2.3 g at a yield of 47.6%. The analytical results on the target compound are given below.

$^1$H-NMR (CDCl$_3$/Me$_4$Si) δ: 1.17(t, J=7.1 Hz, 3H), 1.47 (m, 4H), 1.83(m, 2H), 2.42(s, 3H), 3.15(m, 2H), 3.15(m, 2H), 3.08(d, J=8.6 Hz), 4.10(m, 2H), 4.79(br, 1H), 5.10(s, 2H), 5.14(m, 1H), 7.0–7.4(m, 13H)

$^{13}$C-NMR (CDCl$_3$/Me$_4$Si) δ: 13.99, 21.34, 21.56, 29.41, 32.33, 40.66, 55.36, 61.34, 66.60, 83.03, 127.51, 127.79, 128.06, 128.52, 128.56, 128.92, 129.49, 133.82, 134.43, 136.70, 144.19, 156.37, 170.54

Mass m/z: 554(M+), 510, 382, 338, 292, 274, 248, 200, 173, 155, 108, 91

Example 31

Synthesis of methyl 7-(N-benzyloxycarbonylamino)-3-p-toluenesulfonyloxy-2-phenylheptanoate The same procedures as in Example 30 were performed except that 27.2 g (70.4 mmol) of methyl 7-(N- benzyloxycarbonylamino)-3-hydroxy-2-phenylheptanoate obtained in Example 9 was dissolved in 136 ml of pyridine; 1.27 g (10.39 mmol) of dimethylaminopyridine was added; and 20.1 g (105.6 mmol) of p-toluenesulfonyl chloride was added; to prepare the target compound as a pale yellow oil in an amount 23.5 g at a yield of 61.8%. The analytical results on the target compound are given below.

$^1$H-NMR (CDCl$_3$/Me$_4$Si) δ: 1.45(m, 4H), 1.81(m, 2H), 2.37(s, 3H), 3.14(m, 2H), 3.63(s, 3H), 3.85(d, J=8.5 Hz, 1H), 4.82(br, 1H), 5.10(s, 2H), 5.14(m, 1H), 7.0–7.4(m, 13H)

$^{13}$C-NMR (CDCl$_3$/Me$_4$Si) δ: 21.36, 21.55, 29.38, 32.32, 40.62, 52.35, 55.17, 60.38, 66.57, 82.96, 127.52, 127.86, 128.05, 128.51, 128.59, 128.96, 129.51, 133.79, 134.25, 136.70, 144.24, 156.38, 171.02, 171.12

Mass m/z: 554(M+), 496, 368, 324, 260, 234, 200, 173, 108, 91

Application Example 1

Synthesis of methyl 2-phenyl-2-(2'-pyperidyl)acetate 10.6 g (19.1 mmol) of methyl 7-(N-benzyloxycarbonylamino)-3-p-toluenesulfonyloxy-2-phenylheptanoate prepared in Example 31 and 1.06 g of 5% Pd—C were placed in an autoclave. To the mixture were added 5.6 ml (98 mmol) of acetic acid and 100 ml of methanol. After air in the autoclave was replaced with hydrogen gas, the mixed solution was reacted at room temperature under a hydrogen pressure of 10 kg/cm² for 3 hours. After the completion of the reaction was confirmed by means of HPLC, Pd—C was separated by filtration with a Celite. The supernatant was concentrated under reduced pressure. The filtrate was dissolved in 100 ml of methanol. 6.78 g (49 mmol) of potassium carbonate was added to the mixed solution and the mixture was reacted under heat with refluxing for 18 hours. The reaction solution was concentrated under reduced pressure. The residue was extracted by adding ethylacetate and purified water. The organic layer was dried with magnesium sulfate anhydride and concentrated under reduced pressure. The resulting residue was then purified by means of SGIC (eluent: hexane/ethylacetate/methanol=2/2/1 by volume) to prepare the target compound as a pale yellow oil in an amount of 3.45 g at a yield of 77.5%. The products were analyzed by means of HPLC. As a result, the selectivity of the product in terms of the rate of the threo-form to the erythro-form was 3:7. The analytical results on the target compound are given below.

$^1$H-NMR (CDCl$_3$/Me$_4$Si) δ: 1.1–1.9(m, 6H), 2.49(dt, J=11.2 Hz, J=3.4 Hz, 0.7H), 2.70(dt, J=11.8 Hz, J=3.2 Hz, 0.3H), 2.80–3.10(m, 3H), 3.64(s, 3H), 7.20–7.38(m, 5H)

Mass m/z: 233(M+), 150, 118, 84, 55

Application Example 2

Synthesis of ethyl 2-phenyl-2-(2'-pyperidyl)acetate

The same procedures as in Example 30 were performed except that 0.6 g (19.1 mmol) of ethyl 7-(N-benzyloxycarbonylamino)- 3-p-toluenesulfonyloxy-2-phenylheptanoate prepared in Example 30 and 0.6 g of 5% Pd—C were placed in an autoclave, 15 ml of methanol was added, the resulting residue from the filtrates of the reaction mixture was dissolved in 15 ml of methanol and 290 g(2.1 mmol) of pottasium carbonate was added, to prepare the target compound as a pale yellow oil in an amount of 130 mg at a yield of 49.2%. The selectivity of the product in terms of the rate of the threo-form to the erythro-form was 4:6. The analytical results on the target compound are given below.

$^1$H-NMR (CDCl$_3$/Me$_4$Si) δ: 1.17, 1.21 (t, J=7.2 Hz, J=7.1 Hz 3H), 1.1–1.85(m, 6H), 2.50(dt, J=11.8 Hz, J=2.8 Hz, 0.60H), 2.71(dt, J=11.9 Hz, J=2.9 Hz , 0.40H), 2.90–3.20(m, 2H), 3.44, 3.46(d, J=10.1 Hz, 1H), 4.06, 4.17(m, 2H), 7.20–7.45(m, 5H)

$^{13}$C-NMR (CDCl$_3$/Me$_4$Si) δ: 14.07, 14.13, 24.34, 24.48, 25.78, 26.01, 29.85, 30.99, 46.89, 47.05, 58.44, 58.69, 58.99, 59.09, 60.71, 60.85, 127.46, 127.80, 128.59, 128.61, 128.71, 128.83, 136.23, 136.58, 172.59, 173.37

Mass m/z: 2458(M+), 164, 118, 84

As is clear from the above results, the 7-(N-substituted amino)-3-benzenesulfonyloxy-2-phenylheptanoate derivative represented by formula (3) can be prepared from the 7-(N-substituted amino)-3-oxo-phenylheptanoate derivative represented by the formula (1) via the 7-(N-substituted amino)-3-hydroxy-2-phenylheptanoate derivative represented by formula (2) with ease. Also, from the 7-(N-substituted amino)-3-benzenesulfonyloxy-2-phenylheptanoate represented by formula (3), a 2-phenyl-2-(2'-piperidinyl)acetate derivative such as the compound represented by formula (9), which is quite important for a major intermediate of an antidepressant, can be prepared with ease.

What is claimed is:

1. A 7-(N-substituted amino)-3-(substituted)-2-phenylheptanoate derivative represented by the following 1 formula (1):

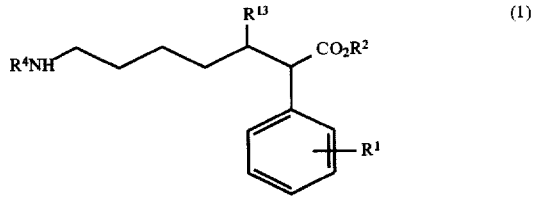

wherein R$^1$ represents a hydrogen atom, a lower alkyl group having 1 to 4 carbon atoms, or a lower alkoxy group having 1 to 4 carbon atoms; R$^2$ represents a lower alkyl group having 1 to 4 carbon atoms; R$^4$ represents a hydrogen atom or a protective group for an amino group; and R$^{13}$ represents a keto group, a hydroxy group or a benzenesulfonyloxy group which may contain a substituted group.

2. A 7-(N-substituted amino)-3-(substituted)-2-phenylheptanoate derivative as claimed in claim 1, wherein said derivative is a compound represented by the following formula (2);

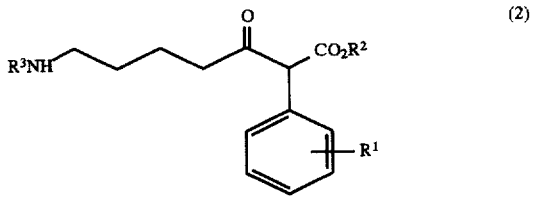

wherein R$^1$ represents a hydrogen atom, a lower alkyl group having 1 to 4 carbon atoms, or a lower alkoxy group having 1 to 4 carbon atoms; R$^2$ represents a lower alkyl group having 1 to 4 carbon atoms; and R$^3$ represents a protective group for an amino-group.

3. A 7-(N-substituted amino)-3-(substituted)-2-phenylheptanoate derivative as claimed in claim 1, wherein said derivative is a compound represented by the following formula (3):

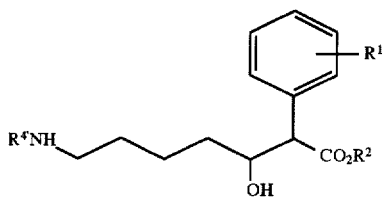

wherein $R^1$ represents a hydrogen atom, a lower alkyl group having 1 to 4 carbon atoms, or a lower alkoxy group having 1 to 4 carbon atoms; $R^2$ represents a lower alkyl group having 1 to 4 carbon atoms; and $R^4$ represents a hydrogen atom or a protective group for an amino group.

4. A 7-(N-substituted amino)-3-(substituted)-2-phenylheptanoate derivative as claimed in claim 1, wherein said derivative is a compound represented by the following formula (4):

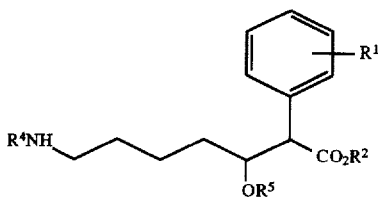

wherein $R^1$ represents a hydrogen atom, a lower alkyl group having 1 to 4 carbon atoms, or a lower alkoxy group having 1 to 4 carbon atoms; $R^2$ represents a lower alkyl group having 1 to 4 carbon atoms; $R^4$ represents a hydrogen atom or a protective group for an amino group; and $R^5$ represents a benzenesulfonyl group which may contain a substituted group.

5. A process for manufacturing a 7-(N-substituted amino)-3-oxo-2-phenylheptanoic acid derivative represented by the following formula (2):

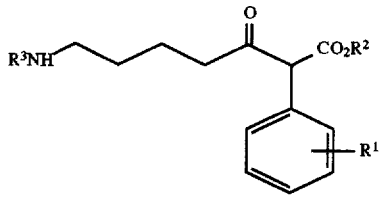

wherein $R^1$ represents a hydrogen atom, a lower alkyl group having 1 to 4 carbon atoms, or a lower alkoxy group having 1 to 4 carbon atoms; $R^2$ represents a lower alkyl group having 1 to 4 carbon atoms; and $R^3$ represents a protective group for an amino group, which comprises a step of reacting an enolate of phenylacetates with an imidazolide by condensation, said derivative is represented by the following formula (6):

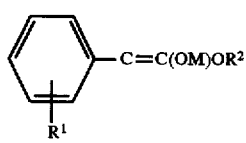

wherein $R^1$ and $R^2$ are the same groups as defined above, and M represents a lithium atom and said imidazolide is represented by the following formula

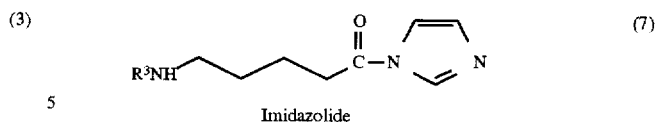

wherein $R^3$ represents a protective group for an amino group.

6. A process for manufacturing a 7-(N-substituted amino)-3-hydroxy-2-phenylheptanoate derivative represented by the following formula (3):

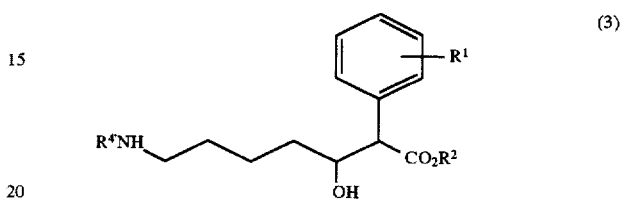

wherein $R^1$ represents a hydrogen atom, a lower alkyl group having 1 to 4 carbon atoms, or a lower alkoxy group having 1 to 4 carbon atoms; $R^2$ represents a lower alkyl group having 1 to 4 carbon atoms; and $R^4$ represents a hydrogen atom or a protective group for an amino group, which comprises a step of reducing a 7-(N-substituted amino)-3-oxo-2-phenylheptanoate derivative represented by the following formula (2):

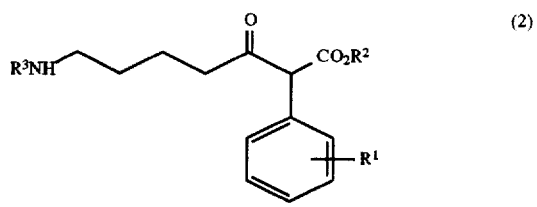

wherein $R^1$ and $R^2$ are the same groups as defined above, and $R^3$ represents a protective group for an amino group.

7. A process for manufacturing a 7-(N-substituted amino)-3-hydroxy-2-phenylheptanoate derivative as claimed in claim 6, wherein said derivative of formula(2) is reacted with hydrogen in the presence of a complex of the VIII group transition metal, of the following formula (8):

wherein $M^1$ represents a ruthenium atom, iridium atom, or rhodium atom; L represents an optically active phosphine ligand; X represents a hydrogen atom, halogen atom, and carboxylic acid derivative residue; Q represents ethylene, 1,5-octadiene, benzene, p-cymene, mesitylene, and the like; Y represents an anion selected from a group consisting of $ClO_4^-$, $BF_4^-$, and $PF_6^-$; m, n, and s respectively denote an integer of 1 or 2; r denotes an integer of 0 or 1; and q denotes an integer of from 0 to 2.

8. A process for manufacturing a 7-(N-substituted amino)-3-hydroxy-2-phenylheptanoate derivative as claimed in claim 6, wherein said derivative of formula (2) is reacted with hydrogen in the presence of a chemical reducing agent.

9. A process for manufacturing a 7-(N-substituted amino)-3-benzenesulfonyloxy-2-phenylheptanoate derivative represented by the following formula (4):

23

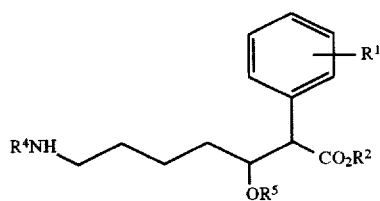

(4)

wherein $R^1$ represents a hydrogen atom, a lower alkyl group having 1 to 4 carbon atoms, or a lower alkoxy group having 1 to 4 carbon atoms; $R^2$ represents a lower alkyl group having 1 to 4 carbon atoms; $R^4$ represents a hydrogen atom or a protective group for an amino group; and $R^5$ represents a benzenesulfonyl group which may contain a substituted group, which comprises

24 a step of reacting a 7-(N-substituted amino)-3-hydroxy-2-phenylheptanoate derivative represented by the following formula (3) with a benzenesulfonyl compound in the presence of a pyridine derivative:

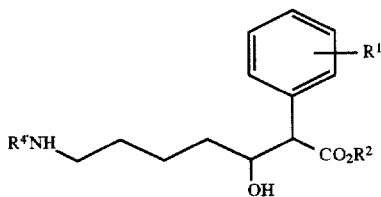

wherein $R^1$, $R^2$ and $R^4$ are the same groups as defined above.

* * * * *